(12) United States Patent
Peetermans et al.

(10) Patent No.: US 6,756,040 B2
(45) Date of Patent: Jun. 29, 2004

(54) VACCINE COMPOSITION COMPRISING A POLYSACCHARIDE CONJUGATE ANTIGEN ADSORBED ONTO ALUMINUM PHOSPHATE

(75) Inventors: Julien Peetermans, Rixensart (BE); Pierre Hauser, Chaumont-Gistoux (BE)

(73) Assignee: SmithKline Beecham Biologicals s.a., Rixensart (BE)

(*) Notice: Subject to any disclaimer, the term of this patent is extended or adjusted under 35 U.S.C. 154(b) by 0 days.

(21) Appl. No.: 10/155,052

(22) Filed: May 23, 2002

(65) Prior Publication Data

US 2002/0182226 A1 Dec. 5, 2002

Related U.S. Application Data

(63) Continuation of application No. 09/951,657, filed on Sep. 13, 2001, now abandoned, which is a continuation of application No. 09/522,234, filed on Mar. 9, 2000, now abandoned, which is a continuation of application No. 08/983,271, filed as application No. PCT/EP96/02690 on Jun. 19, 1996, now abandoned.

(30) Foreign Application Priority Data

Jun. 23, 1995 (GB) ............................................. 9512827
Jul. 1, 1995 (GB) ............................................. 9513443
Dec. 15, 1995 (GB) ............................................. 9525657
Mar. 22, 1996 (GB) ............................................. 9606032

(51) Int. Cl.[7] .......................................... A61K 39/295
(52) U.S. Cl. ............................. 424/201.1; 424/196.11; 424/197.11; 424/193.1; 424/203.1; 424/204.1; 424/226.1; 424/227.1; 424/217.1; 424/234.1; 424/236.1; 424/239.1; 424/256.1; 514/54
(58) Field of Search .......................... 424/197.11, 203.1, 424/196.11, 201.1, 193.1, 204.1, 226.1, 227.1, 217.1, 234.1, 236.1, 239.1, 256.1; 514/54

(56) References Cited

U.S. PATENT DOCUMENTS 5,897,867 A 4/1999 Eckhardt et al.

FOREIGN PATENT DOCUMENTS

| AU | 708777 | 5/1996 |
|---|---|---|
| EP | 0 208 375 | 1/1987 |
| EP | 0 594 950 | 5/1994 |
| WO | WO 93/24148 | 12/1993 |
| WO | WO 96/37222 | 11/1996 |
| WO | WO 99/48525 | 9/1999 |

OTHER PUBLICATIONS

Makela, et al., *J. Immunol.*, 139: 1999–2004 (1987).
Tarkowski, et al., *J. Immunol.*, 144: 3770–3778 (1990).
Audibert, et al., *Infect. Immun.*, 45: 261–266 (1984).
M.F. Powell, Plenum Press, NY, Chapter 7. "A Compendium of Vaccine Adjuvants and Excipients", (1995).

Vella, et al., *Biotechnology*, 20: 1–22 (1992).
Schneerson, et al., *Infect. Immun.*, 52(2): 519–28 (1986).
Claesson, et al., "Clinical and Immunologic Responses to the Capsular Polysaccharide of *Haemophilus influenzae* Type B Alone or Conjugated to Tetanus Toxoid in 18– to 23–month old Children", *The Journal of Pediatrics*, 112: 695–702 (1988).
Bixler, et al., "Augmentation by Interleukins of the Antibody Response to a Conjugate Vaccine Against *Haemophilus Influenzae* B", *Adv. Exp. Med. Biol.*, 303: 185–190, (1991). *Immunobiology of Proteins and Peptides VI*, Ed.: M.Z. Atassi, Plenum Press New York.
Peeters, et al., "Synthetic Trimer and Tetramer of 3–β–D–Ribose–(1–1)–D–Ribitol–5–Phosphate Conjugated to Protein Induce Antibody Responses to *Haemophilus influenzae* Type b Capsular Polysaccharide in Mice and Monkeys". *Infection and Immunity*, 60(5): 1826–1833 (1992).
Watemberg, et al., "Safety and Immunogenicity of *Haemophilus* Type b–Tetanus Protein Conjugate Vaccine, Mixed in the Same Syringe with Diphtheria–Tetanus–Pertussis Vaccine in Young Infants". *Pediatr. Infect. Dis. J.*, 10(10):758–761 (1991).
Siber, et al., "Development of a Guinea Pig Model to Assess Immunogenicity of *Haemophilus influenzae* Type b Capsular Polysaccharide Conjugate Vaccines". *Vaccine*, 13(6): 525–531 (1995).
Scheifele, et al., "Can *Haemophilus influenzae* Type b–Tetanus Toxoid Conjugate Vaccine be Combined with Diphtheria Toxoid–Pertussis Vaccine–Tetanus Toxoid?" *Can. Med. Assoc. J.*, 149(8): 1105–1112 (1993).
"Recommendations for Use of *Haemophilus* b Conjugate Vaccines and a Combined Diphtheria, Tetanus, Pertussis, and *Haemophilus* b Vaccine". *MMWR*, 42: RR–13 (1993).
Paradiso, et al., "Safety and Immunogenicity of a Combined Diphtheria, Tetanus, Pertussis and *Haemophilus influenzae* Type b Vaccine in Young Infants". *Pediatrics*, 92(6): 827–832 (1993).
Black, et al., "Safety of Combined Oligosaccharide Conjugate *Haemophilus influenzae* Type b (HbOC) and Whole Cell Diphtheria–Tetanus Toxoids–Pertussis Vaccine in Infancy". *Pediatr. Infect. Dis. J.*, 12:981–985 (1993).

(List continued on next page.)

*Primary Examiner*—Donna C. Wortman
(74) *Attorney, Agent, or Firm*—Jeffrey A. Sutton; Stephen Venetianer; Charles M. Kinzig

(57) ABSTRACT

The invention relates to a vaccine formulation for the prevention of Haemophilus Influenzae Type B (Hib) infections and where the antigen is adsorbed onto aluminum phosphate. The invention also relates to a multivalent vaccines, that is a vaccine for the amelioration or treatment of more than one disease states. The present invention also relates to the production and use of such vaccines in medicine.

11 Claims, No Drawings

OTHER PUBLICATIONS

Approved Datasheet for Tetramune from www.ias.org.nz, dated Jun. 26, 1996.

Public Product Record for PedvaxHIB from www.biopharma.com, 2001.

Calandra, et al., "Anti–PRP Antibody Levels After a Primary Series of PRP–OMPC and Persistence of Antibody Titres Following Primary and Booster Doses". *Vaccine*, 11(S1): S58–S62 (1993).

Mulholland, et al., "Safety and Immunogenicity of *Haemophilus influenzae* Type B–*Neisseria meningitidis* Group B Outer Membrane Protein Complex Conjugate Vaccine Mixed in the Syringe with Diphtheria–Tetanus–Pertussis Vaccine in Young Gambian Infants". *Pediatr. Infect. Dis. J.*, 12: 632–637 (1993).

West, et al., "Immunogenicity of a Bivalent Haemophilus Influenzae Type B/Hepatitis B (HIB/HB) Vaccine". *Pediatr. Res.*, 35(4Pt2): 17A(88) 1994.

Press Release by Merck & Co., Sept. 1996.

West, et al., "Safety and Immunogenicity of a Bivalent *Haemophilus influenzae* Type b/Hepatitis B Vaccine in Healthy Infants". *Pediatr. Infect. Dis. J.*, 16: 593–599 (1997).

Avendano, et al., "*Haemophilus influenzae* Type b Polysaccharide–Tetanus Protein Conjugate Vaccine Does Not Depress Serologic Responses to Diphtheria–Tetanus–Pertussis Antigens when Coadministered in the same Syringe with Diphtheria–Tetanus–Pertussis Vaccine at Two, Four and Six Months of Age". *Pediatr. Infect. Dis. J.*, 12: 638–643 (1993).

Kaplan, et al., "Immunogenicity and Safety of *Haemophilus influenzae* Type b–Tetanus Protein Conjugate Vaccine Alone or Mixed with Diphtheria–Tetanus–Pertussis Vaccine in Infants". *J. Pediatr.*, 124: 323–327 (1994).

Miller, et al., "Safety and Immunogenicity of PRP–T Combined with DTP: Excretion of Capsular Polysaccharide an Antibody Response in the Immediate Post–Vaccination Period". *Pediatr.*, 95(4): 522–527 (1995).

Corbel. "Reasons for Instability of Bacterial Vaccines". *Dev. Biol. Stand.*, 87: 113–124 (1996).

F. Brown. "New Approaches to Stabilisation of Vaccines Potency". *Karger Publisher Website at* www.karger.ch (2001).

VACCINE COMPOSITION COMPRISING A POLYSACCHARIDE CONJUGATE ANTIGEN ADSORBED ONTO ALUMINUM PHOSPHATE

This is a continuation of application Ser. No. 09/951,657, filed Sep. 13, 2001, abandoned, which is a continuation of application Ser. No. 09/522,234, filed Mar. 9, 2000, abandoned which is a continuation of Continued Prosecution application Ser. No. 08/983,271, filed Feb. 11, 1998, abandoned which is a is a §371 of International Application No. PCT/EP96/02690, filed Jun. 19, 1996, which claims priority of foreign Application Nos. GB 9512827.8, filed Jun. 23, 1995; GB 9513443.3, filed Jul. 1, 1995; GB 9525657.4, filed Dec. 15, 1995; and GB 9606032.2, filed Mar. 22, 1996.

The present invention relates to new vaccine formulations, comprising a conjugated polysaccharide antigen linked to a carrier protein. In particular the invention relates to a vaccine formulation for the prevention of Haemophilus Influenzae Type B (Hib) infections and where the antigen is adsorbed on to aluminium phosphate. The invention also relates to a multivalent vaccine, that is a vaccine for the amelioration or treatment of more than one disease states. The present invention also relates to the production and use of such vaccines in medicine.

Vaccines that utilise polysaccharides are known in the art. For example a vaccine for the prevention of Haemophilus influenzae b (Hib) infections are based on the capsular polysaccharide (PRP) conjugated with a carrier protein. The polysaccharide is a polymer of ribose, ribitol and phosphate. These vaccines are typically presented as plain (ie without adjuvantation) formulations. Although in one case, (Pedvax Hib produce by Merck) a diluent containing aluminium hydroxide is utilised to reconstitute the lyophilised conjugate. Typically the carrier protein is a diphtheria or tetanus toxoid or an outer membrane protein of N. menigitidis. Examples of such conjugate vaccine antigens are disclosed in U.S. Pat. Nos. 4,365,170, 4,673,574, EP 208 375, EP 477508 and EP 161 188.

It is desirable to administer such conjugate vaccines with other antigens or vaccines at the same fine and this can involve multiple injections. Problems associated with multiple injections include a more complicated administration procedure and a large total injection volume. This is a particularly acute problem when the vaccine is intended for infants.

It has therefore been proposed to produce combination vaccines. One well known combination vaccine provides protection against Diphtheria, tetanus and B. pertussis infections. This vaccine comprises a whole cell or an accellular pertussis component which typically consists of two or three antigens—(detoxified PT, FHA and often, but not exclusively 69 kDa) although in certain circumstances other B. pertussis antigens may also be present and toxoided diphtheria and tetanus toxins. Such vaccines are often referred to as DTPw or DTPa. Other antigens would desirable be added to such a combination vaccine for the prevention of diseases like hepatitis B. or Polio.

It would be desirable to add polysaccharide conjugate vaccines to such a combination. However we have found that simple mixing of the components results in a reduction of antibody titres to the polysaccharide component.

The present inventors have discovered that this reduction can be inhibited if the conjugate antigen is adsorbed on to aluminium phosphate. In contrast, if the antigen is adsorbed on to aluminium hydroxide, there is a complete reduction of antibody titres to the polysaccharide component.

Accordingly the present invention provides a vaccine composition comprising a polysaccharide conjugate antigen adsorbed on to aluminium phosphate. Preferably the antigen is capsular polysaccharide (PRP) from Hib conjugated with a carrier protein.

Preferably the carrier protein is either diphtheria or tetanus toxoid, Diphtheria $Crm_{197}$ protein or an outer membrane protein from a bacteria such as N. meningitidis.

The polysaccharide conjugate may be prepared by any known coupling technique. For example the polysaccharide can be coupled via a thioether linkage. This conjugation method relies on activation of the polysaccharide with 1-cyano-4-dimethylamino pyridinium tetrafluoroborate (CDAP) to form a cyanate ester. The activated polysaccharide may thus be coupled directly or via a spacer group to an amino group on the carrier protein. Preferably, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 Uniformed Services University.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide activated polysaccharide derivatised with adipic acid hydrazide (ADH) to the protein carrier by carbodiimide condensation. Such conjugation is described in Chu C. et al Infec Immunity, 1983 245 256.

In a preferred embodiment of the invention the ratio of PRP polysaccharide to carrier protein is reduced from a typical 1:3 to 1:0.3 to 1:2. Such low ratio conjugates are advantageous, since even in an unadjuvanted state, they do not suffer from interference problems.

In a preferred embodiment of the invention the formulation preferably contains at least one other component selected from antigens which afford protection against one or more of the following: Hepatitis A virus (HAV), diphtheria, tetanus, pertussis, Hepatitis B and polio.

Particular combination vaccines within the scope of the invention include a DTPa (diphtheria-tetanus-accellular pertussis)-Hib combination vaccine formulation, an Hib-Hepatitis B vaccine formulation, a DTPa-Hib-Hepatitis B vaccine formulation and an IPV (inactivated polio vaccine)-DTPa-Hib-Hepatitis B vaccine formulation.

The above combinations may optionally include a component which is protective against Hepatitis A.

Suitable components for use in such vaccines are already commercially available and details may be obtained from the World Health Organization. For example the IPV component may be the Salk inactivated polio vaccine. The Diphtheria, Tetanus and Pertussis vaccine may comprise an acellular product such as Infanrix DTPa (SmithKline Beecham Biologicals). The component affording protection against Hepatitis A is preferably the product known as 'Havrix' (SmithKline Beecham Biologicals) which is a killed attenuated vaccine derived from the HM-175 strain of HAV [see 'Inactivated Candidate Vaccines for Hepatitis A' by F. E. Andre, A Hepburn and E. D'Hondt, *Prog Med. Virol.* Vol. 37, pages 72–95 (1990) and the product monograph 'Havrix' published by SmithKline Beecham Biologicals (1991)]. The Hepatitis B component may comprise the 'S' antigen as in 'Engerix-B'.

Advantageously the Haemophilus Influenzae B or combination vaccine according to the invention is a paediatric vaccine.

Vaccine preparation is generally described in Vaccine Design—The Subunit and adjuvant approach Ed Powell and Newman; Pellum Press. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of conjugate antigen in each vaccine dose is selected as an amount which induces an immunoprotective response without significant, adverse side effects in typical vaccinees. Such amount will vary depending on which specific immunogens are employed. Generally it is expected that each dose will comprise 1–1000 ug of total immunogen, preferably 2–100 ug, most preferably 4–40 ug. An optimal amount for a particular vaccine can be ascertained by standard studies involving observation of antibody titres and other responses in subjects. Following an initial vaccination, subjects may receive one or two booster injections at about 4 weeks intervals.

In a further aspect according to the invention, there is provided a method of producing the vaccine comprising adsorbing the conjugate antigen on to aluminium phosphate. The adsorbing is preferably done at a pH of between 5 and 6, preferably at about 5.4. In an embodiment the vaccine is freeze dried after standing for more than 24 hours. Alternatively, the vaccine of the invention may be combined with other antigens in a liquid form.

The invention further provides the first medical use of such a vaccine.

In a further embodiment the invention provides a method of preventing or ameliorating Heamophilus Influenzae B infections, the method comprising the administration of a non toxic, effective amount of the vaccine of the invention.

The following examples illustrate the invention.

EXAMPLE 1

Vaccine Formulation Comprising HiB Polysaccharide Conjugated on Tetanus Toxoid Adsorbed on to Aluminium Phosphate.

Synthesis of Haemophilus influenzae Type B Capsular Polysaccharide (PRP) Tetanus Toxoid (TT) Conjugate 1.a Cyanogen Bromide Coupling The covalent binding of PRP and TT is carried out by a coupling chemistry developed at the NIH (Chu C. et al (1983), further studies on the imnunogenicity of Haemophilus influenzae type b and pneumococcal type 6A polysacclaride protein conjugates. Infec. Immunity, 245–256). The PRP is activated under controlled conditions by cyanogen bromide and derivatised with an adipic hydrazide spacer.

After derivatisation, the activated polysaccharide (PRP-AH) is purified by diafiltration. The coupling of the two purified components (PRP-AH and TT) is effected by carbodiimide condensation. The conjugate is then purified by ultrafiltration and gel filtration to remove the reagent and unconjugated PRP and TT.

Synthesis of PRP-TT Conjugates 1.b CDAP coupling 30 mg of native Hib PRP were dissolved in 6 ml 2M NaCl. 225 mcl of CDAP (1 cyano-4-dimethylamino-pyridinum tetrafluoroborate) was added to the polysaccharide solution (from a 100 mg/ml stock solution in acetonitrile). 90 seconds later, 450 mcl of 0.2 M triethylamine was added. The activation was performed at pH 10.0 during 1 minute on ice and minute at room temperature.

90 mg of tetanus toxoid (initial PS/protein ratio of 1/3) were added to the activated polysaccharide and the coupling reaction was performed at room temperature for 1 hour. Then, the reaction was quenched with 3 ml of 1M glycine solution, pH 5.0 for 30 minutes at room temperature and overnight at 4° C.

The conjugate was purified by gel filtration on a sephacryl HR 500 column equilibrated in 0.2M NaCl. The carbohydrate and protein content was determined in each fraction. The conjugate was pooled and sterile filtered (membrane Minisart ⊕0.222 γm).

Adsorption on to Aluminium Phosphate 1.c To 0.15 mg of aluminium phosphate was added 12.5 mcg of the polysaccharide conjugate of example 1(a). This was stirred for two hours the pH is adjusted to 5.1. The mixture was left to stand for one day at room temperature and the adsorbed conjugate then left for a further 9 days at 2 to 8° C. To prepare a freeze dried product the adsorbed product is diluted in lactose (15.75 mg) to give a final composition of 25 mcg polysaccharide/ml and 0.4 mg Al/ml and the resulting composition was filled into 0.5 ml vials and freezed dried.

To prepare a liquid product the adsorbed conjugate is diluted in water for injection with 150 mM NaCl and 5 mg/ml phenoxy ethanol to give a final composition of 20 mcg polysaccharide/ml and 0.32 mg Al/ml.

1.d Formulation of a Diphtheria Tetanus and Pertussis (acellular) vaccine with and without hepatitis B was done in accordance to the methods of WO 93/24148 (SmithKline Beecham Biologicals).

1.e Preparation of a 'low ratio' PRP-TT aluminum phosphate pre-adsorbed conjugate.

The conjugate was prepared in an analogous manner to the example of 1a, but with reduced amount of Tetanus used (30 mcg, 60 mcg) to give a product with Polysaccharide:Protein ratio of 1:1 or 1:2. The conjugate is then adsorbed on to aluminium phosphate according to the method of example 1c. The final freeze dried preparation contains 12.5 $\mu$g of conjugate, 0.15 mg ALPO$_4$, 15.75 mg lactose. This is reconstituted in 0.5 ml water for injection prior to use at a pH of 0.1+/−0.1.

EXAMPLE 2

Immunogenicity of PRP-TT Conjugate Preadsorbed on Aluminium Phosphate and Combined with DTPa or DTPa-HB The Hib conjugate of example 1a), either plain or preadsorbed on Al PO4 (both vaccines were lyophilized) was mixed with DTPa or DTPa HB no more than 1 hour before injection and the combination was injected in baby rats (1 week of age) by the subcutaneous route at a dose corresponding to ½0th a human dose (0.5 $\mu$g of PRP). The rats were boosted 2 weeks and 4 weeks later and the serum was collected was collected after each immunization to measure anti-PRP antibodies. Controls included the Hib vaccines (adsorbed or not on Al PO4) reconstituted in saline.

Groups of 10 randomized baby rats (1 week of ago-OFA strain) were immunized 3 times subcutaneously at 0–14–28 days with ½0th human dose of Hib vaccine, alone or combined with DTPa or DTPa HB (½0th a human dose). The reconstitution of the lyophilised Hib vaccine with saline or combinations (DTPa or DTPa HB) was done less than 1 hour before immunization.

The rats were bled under anesthesia at 14–28–42 and 56 days. The anti-PRP antibodies were measured by ELISA in individual sera and the titers were expressed in γ/ml using a calibrated reference. The GMT was calculated for each group and for each time point. The 95% confidence limits were calculated for the titers obtained after that third immunization.

As shown in table 1, the adsorption of Hib conjugate on Al PO4 does not modify its imnunogenicity: some anti-PS were produced after the second dose and a good booster effect is shown after the third dose as seen in human babies. The mixing of Hib vaccine with DTPa or DTPa HB reduces by 3 to 8 fold the anti-PRP response and, in the case of DTPa-HB, this decrease is significant. In contrast, the pre-adsorption of the Hib vaccine on Al PO4 restores the anti-PRP response to a level at least equivalent to that obtained with the plain vaccine.

Conclusion:

The Hib/aluminium phosphate formulation has thus the potential to solve the compatibility problem encountered when mixing Hib with other peadiatric combinations.

TABLE 1

Immunogenicity in a baby rat model of PRP-TT conjugate pre adsorbed on AlPO4 and combined with DTPa or DTPa-HB

| Vaccine | Anti-PRP titre (γ/ml) at day | | | |
|---|---|---|---|---|
| | 14 (Post I) | 28 (Post II) | 42 (Post III) | 56 (Post III 30) |
| None (Nacl 0.9%) | <0.05 | <0.05 | <0.05 | <0.05 |
| Hib-001 | <0.05 | 0.06 | 12.9 (4–37) | 10.9 (4–31) |
| Hib/AlPO4 (Dhib-024) | <0.05 | 1.3 | 11.8 (5–29) | 15.4 (7–35) |
| Hib-001 + DTPa (119) | <0.05 | 0.16 | 3.4 (0–28) | 1.4 (0.1–17) |
| Hib/AlPO4 + DTPa (119) | <0.05 | 1.9 | 20.9 (7–59) | 19.7 (9.42) |
| Hib-001 + DTPa HB (16705) | <0.05 | 0.14 | 2.8 (1–6) | 3.9 (2–9) |
| Hib/AlPO4 + DTPa HB (16705) | <0.05 | 0.47 | 11.4 (5–27) | 18.1 (9–38) |
| Hib/Al(OH$_3$) | <0.05 | <0.05 | <0.05 | <0.14 |

We claim:

1. A combination vaccine comprising a capsular polysaccharide of Haemophilus influenzae B conjugated to a carrier protein, admixed with diphtheria toxoid, tetanus toxoid, pertussis antigens, and one or more other antigens selected from the group: Hepatitis A virus, Hepatitis B surface antigen and Inactivated Polio Virus; wherein the conjugate is adsorbed onto aluminum phosphate.

2. A combination vaccine according to claim 1, wherein the carrier protein is selected from the group consisting of: diphtheria toxoid, Diphtheria CRML197 protein and Meningococcal outer membrane protein.

3. A combination vaccine according to claim 1 wherein the carrier protein conjugated to the capsular polysaccharide of Haemophilus influenzae B is tetanus toxoid.

4. A combination vaccine according to claim 1 wherein the ratio of the Haemophilus influenzae B polysaccharide to carrier protein is from 1:0.3 to 1:2 (w:w).

5. A combination vaccine according to claim 1 wherein the adsorbed conjugate has been freeze-dried.

6. A combination vaccine according to claim 5 wherein the adsorbed, freeze-dried conjugate is suspended in water for injection.

7. A method of producing a vaccine according to claim 1 comprising conjugating a capsular polysaccharide of Haemophilus influenzae B antigen to a protein carrier, adsorbing said conjugate onto aluminum phosphate, and admixing with diphtheria toxoid, tetanus toxoid, pertussis antigens, and one or more other antigens selected from the group consisting of: Hepatitis A virus, Hepatitis B surface antigen and Inactivated Polio Virus.

8. A method of treating a patient suffering from or susceptible to Haemophilus influenzae B infection, comprising administering a safe and efficacious amount of a vaccine composition according to claim 1.

9. A kit comprising a container of freeze-dried vaccine comprising a capsular polysaccharide of Haemophilus influenzae B conjugated to a carrier protein and adsorbed onto aluminum phosphate, and a second container comprising antigens to diphtheria toxoid, tetanus toxoid, pertussis antigens, and one or more other antigens selected from the group: Hepatitis A virus, Hepatitis B surface antigen and Inactivated Polio Virus.

10. A combination vaccine comprising a capsular polysaccharide of Haemophilus influenzae B conjugated to tetanus toxoid and adsorbed onto aluminum phosphate, in combination with the following antigens: diphtheria toxoid, tetanus toxoid, acellular pertussis antigens, Hepatitis B surface antigen and Inactivated Polio Virus.

11. A combination vaccine comprising a capsular polysaccharide of Haemophilus influenzae B conjugated to tetanus toxoid and adsorbed onto aluminum phosphate, in combination with the following antigens: diphtheria toxoid, tetanus toxoid, whole-cell pertussis, and Hepatitis B surface antigen.

* * * * *